United States Patent
Lim

(10) Patent No.: US 8,945,171 B2
(45) Date of Patent: Feb. 3, 2015

(54) DELIVERY SYSTEM FOR IMPLANTABLE DEVICES

(75) Inventor: Chhuon Lim, Santa Ana, CA (US)

(73) Assignee: Covidien LP, Mansfield, MA (US)

( * ) Notice: Subject to any disclaimer, the term of this patent is extended or adjusted under 35 U.S.C. 154(b) by 606 days.

(21) Appl. No.: 13/249,223

(22) Filed: Sep. 29, 2011

(65) Prior Publication Data
US 2013/0085521 A1    Apr. 4, 2013

(51) Int. Cl.
*A61M 29/00*    (2006.01)
*A61B 17/12*    (2006.01)

(52) U.S. Cl.
CPC ..... *A61B 17/12113* (2013.01); *A61B 17/12154* (2013.01); *A61B 2017/12054* (2013.01)
USPC .......................................................... 606/200

(58) Field of Classification Search
CPC ............................ A61F 2/95; A61F 2002/011
USPC .......... 600/203; 606/108, 191, 194, 198, 200; 623/1.11
See application file for complete search history.

(56) References Cited

U.S. PATENT DOCUMENTS

| | | | |
|---|---|---|---|
| 5,109,867 A | 5/1992 | Twyford, Jr. | |
| 5,217,484 A | 6/1993 | Marks | |
| 5,234,437 A | 8/1993 | Sepetka | |
| 5,250,071 A | 10/1993 | Palermo | |
| 5,261,916 A | 11/1993 | Engelson | |
| 5,263,964 A | 11/1993 | Purdy | |
| 5,282,806 A | 2/1994 | Haber et al. | |
| 5,304,195 A | 4/1994 | Twyford, Jr. et al. | |
| 5,312,415 A | 5/1994 | Palermo | |
| 5,350,397 A | 9/1994 | Palermo et al. | |
| 5,368,592 A | 11/1994 | Stern et al. | |
| 5,417,708 A | 5/1995 | Hall | |
| 5,480,382 A | 1/1996 | Hammerslag et al. | |
| 5,490,859 A | 2/1996 | Mische et al. | |
| 5,499,985 A | 3/1996 | Hein et al. | |
| 5,562,698 A | 10/1996 | Parker | |
| 5,669,905 A | 9/1997 | Scheldrup et al. | |
| 5,728,129 A | 3/1998 | Summers | |
| 5,800,455 A | 9/1998 | Palermo et al. | |
| 5,814,062 A | 9/1998 | Sepetka et al. | |

(Continued)

FOREIGN PATENT DOCUMENTS

CN    2456640 Y    10/2001
CN    1668250 A    9/2005

(Continued)

OTHER PUBLICATIONS

U.S. Appl. No. 13/249,203, filed Sep. 29, 2011.

*Primary Examiner* — Ashley Fishback
(74) *Attorney, Agent, or Firm* — Elizabeth A. O'Brien, Esq.

(57) ABSTRACT

Medical devices and systems for treating a vascular condition are described. One such device includes a sheath, an elongate delivery member, and a lock. The sheath has a wall that includes an inner surface and an outer surface. The inner surface defines a lumen along the sheath. An access opening is in a proximal portion of the wall and is in fluid communication with the lumen. The delivery member is at least partially disposed within the lumen. The delivery member passes through the access opening. The lock is slidably disposed on an outer periphery of the wall. The lock slidably moves from a first position to a second position along a longitudinal axis of the sheath. The lock positioned in the first position restricts movement of the delivery member.

22 Claims, 4 Drawing Sheets

(56) References Cited

U.S. PATENT DOCUMENTS

| | | |
|---|---|---|
| 5,895,391 A | 4/1999 | Farnholtz |
| 5,980,514 A | 11/1999 | Kupiecki et al. |
| 5,989,242 A | 11/1999 | Saadat et al. |
| 6,004,338 A | 12/1999 | Ken et al. |
| 6,022,369 A | 2/2000 | Jacobsen |
| 6,039,744 A | 3/2000 | Forber |
| 6,063,070 A | 5/2000 | Eder |
| 6,136,015 A | 10/2000 | Kurz et al. |
| 6,152,947 A | 11/2000 | Ambrisco et al. |
| 6,190,373 B1 | 2/2001 | Palermo et al. |
| RE37,117 E | 3/2001 | Palermo |
| 6,203,547 B1 | 3/2001 | Nguyen et al. |
| 6,270,508 B1 | 8/2001 | Klieman et al. |
| 6,375,668 B1 | 4/2002 | Gifford et al. |
| 6,397,850 B1 | 6/2002 | Scheldrup et al. |
| 6,464,699 B1 | 10/2002 | Swanson |
| 6,589,236 B2 | 7/2003 | Wheelock et al. |
| 6,589,251 B2 | 7/2003 | Yee et al. |
| 6,656,351 B2 | 12/2003 | Boyle |
| 6,911,039 B2 | 6/2005 | Shiu et al. |
| 6,953,473 B2 | 10/2005 | Porter |
| 6,964,683 B2 | 11/2005 | Kowalsky et al. |
| 6,994,689 B1 | 2/2006 | Zadno-Azizi et al. |
| 7,018,394 B2 * | 3/2006 | Diaz et al. .................. 606/200 |
| 7,022,133 B2 | 4/2006 | Yee et al. |
| 7,208,003 B2 | 4/2007 | Davis et al. |
| 7,226,460 B2 | 6/2007 | Gibson et al. |
| 7,294,146 B2 | 11/2007 | Chew |
| 7,331,973 B2 | 2/2008 | Gesswein et al. |
| 7,344,558 B2 | 3/2008 | Lorenzo et al. |
| 7,367,987 B2 | 5/2008 | Balgobin et al. |
| 7,371,252 B2 | 5/2008 | Balgobin et al. |
| 7,377,932 B2 | 5/2008 | Mitelberg et al. |
| 7,419,501 B2 | 9/2008 | Chiu et al. |
| 7,591,829 B2 | 9/2009 | Gibson et al. |
| 7,691,124 B2 | 4/2010 | Balgobin |
| 7,708,755 B2 | 5/2010 | Davis, III et al. |
| 7,722,636 B2 | 5/2010 | Farnan |
| 7,722,637 B2 | 5/2010 | Barry et al. |
| 7,753,931 B2 | 7/2010 | Diaz et al. |
| 7,780,693 B2 | 8/2010 | Brady et al. |
| 7,811,305 B2 | 10/2010 | Balgobin et al. |
| 7,901,444 B2 | 3/2011 | Slazas |
| 7,918,872 B2 | 4/2011 | Mitelberg et al. |
| 8,007,509 B2 | 8/2011 | Buiser et al. |
| RE42,758 E | 9/2011 | Ken et al. |
| 8,016,852 B2 | 9/2011 | Ho et al. |
| 8,029,466 B2 | 10/2011 | Wilson et al. |
| 8,034,073 B2 | 10/2011 | Davis, III et al. |
| 8,062,325 B2 | 11/2011 | Mitelberg et al. |
| 8,100,918 B2 | 1/2012 | Gandhi et al. |
| 8,133,252 B2 | 3/2012 | Davis et al. |
| 8,142,456 B2 | 3/2012 | Rosqueta et al. |
| 8,333,796 B2 | 12/2012 | Tompkins et al. |
| 2001/0037141 A1 | 11/2001 | Yee et al. |
| 2002/0010481 A1 | 1/2002 | Jayaraman |
| 2002/0072712 A1 | 6/2002 | Nool et al. |
| 2002/0116024 A1 | 8/2002 | Goldberg et al. |
| 2003/0014073 A1 | 1/2003 | Bashiri et al. |
| 2003/0045901 A1 | 3/2003 | Opolski |
| 2003/0171770 A1 | 9/2003 | Kusleika et al. |
| 2003/0199966 A1 | 10/2003 | Shiu et al. |
| 2004/0002731 A1 | 1/2004 | Aganon et al. |
| 2004/0002733 A1 | 1/2004 | Teoh |
| 2004/0034363 A1 | 2/2004 | Wilson et al. |
| 2004/0087964 A1 | 5/2004 | Diaz et al. |
| 2004/0106946 A1 | 6/2004 | Ferrera et al. |
| 2004/0181256 A1 | 9/2004 | Glaser |
| 2004/0243228 A1 | 12/2004 | Kowalsky et al. |
| 2005/0021023 A1 | 1/2005 | Guglielmi et al. |
| 2006/0025792 A1 | 2/2006 | Gibson et al. |
| 2006/0025801 A1 | 2/2006 | Lulo et al. |
| 2006/0025802 A1 | 2/2006 | Sowers |
| 2006/0036281 A1 | 2/2006 | Patterson et al. |
| 2006/0079926 A1 | 4/2006 | Desai et al. |
| 2006/0106417 A1 | 5/2006 | Tessmer et al. |
| 2006/0116714 A1 | 6/2006 | Sepetka et al. |
| 2006/0200047 A1 | 9/2006 | Galdonik et al. |
| 2006/0271097 A1 | 11/2006 | Ramzipoor et al. |
| 2006/0276823 A1 | 12/2006 | Mitelberg et al. |
| 2006/0276824 A1 | 12/2006 | Mitelberg et al. |
| 2006/0278680 A1 | 12/2006 | Viola et al. |
| 2007/0083219 A1 | 4/2007 | Buiser et al. |
| 2007/0173757 A1 | 7/2007 | Levine et al. |
| 2007/0179520 A1 | 8/2007 | West |
| 2007/0185524 A1 | 8/2007 | Diaz et al. |
| 2007/0221230 A1 | 9/2007 | Thompson et al. |
| 2007/0239193 A1 | 10/2007 | Simon et al. |
| 2007/0239255 A1 | 10/2007 | Hines |
| 2007/0267281 A1 | 11/2007 | Smith |
| 2007/0270936 A1 | 11/2007 | Andreas et al. |
| 2007/0282373 A1 | 12/2007 | Ashby et al. |
| 2008/0045997 A1 | 2/2008 | Balgobin et al. |
| 2008/0097462 A1 | 4/2008 | Mitelberg et al. |
| 2008/0228215 A1 | 9/2008 | Strauss et al. |
| 2008/0243106 A1 | 10/2008 | Coe et al. |
| 2008/0255542 A1 | 10/2008 | Nimgaard et al. |
| 2008/0281350 A1 | 11/2008 | Sepetka et al. |
| 2008/0300616 A1 | 12/2008 | Que et al. |
| 2008/0306504 A1 | 12/2008 | Win et al. |
| 2009/0012554 A1 | 1/2009 | Makower et al. |
| 2009/0018653 A1 | 1/2009 | Bashiri et al. |
| 2009/0024154 A1 | 1/2009 | Williams et al. |
| 2009/0062812 A1 | 3/2009 | Fitz et al. |
| 2009/0088832 A1 | 4/2009 | Chew et al. |
| 2009/0138036 A1 | 5/2009 | Nardone et al. |
| 2009/0163780 A1 | 6/2009 | Tieu |
| 2009/0163986 A1 | 6/2009 | Tieu et al. |
| 2009/0177261 A1 | 7/2009 | Teoh et al. |
| 2009/0182268 A1 | 7/2009 | Thielen et al. |
| 2009/0254169 A1 | 10/2009 | Spenser et al. |
| 2009/0270877 A1 | 10/2009 | Johnson et al. |
| 2009/0287291 A1 | 11/2009 | Becking et al. |
| 2009/0312748 A1 | 12/2009 | Johnson et al. |
| 2010/0004673 A1 | 1/2010 | Denison et al. |
| 2010/0030200 A1 | 2/2010 | Strauss et al. |
| 2010/0094395 A1 | 4/2010 | Kellett |
| 2010/0174269 A1 | 7/2010 | Tompkins et al. |
| 2010/0234872 A1 | 9/2010 | Guo et al. |
| 2010/0256666 A1 | 10/2010 | Chen et al. |
| 2010/0268204 A1 | 10/2010 | Tieu et al. |
| 2010/0268251 A1 | 10/2010 | Chen et al. |
| 2010/0268252 A1 | 10/2010 | Chen et al. |
| 2011/0022003 A1 | 1/2011 | Tekulve |
| 2011/0046657 A1 | 2/2011 | Guo et al. |
| 2011/0106098 A1 | 5/2011 | Williams |
| 2011/0106128 A1 | 5/2011 | Chen |
| 2011/0118772 A1 | 5/2011 | Chen et al. |
| 2011/0118776 A1 | 5/2011 | Chen et al. |
| 2011/0172700 A1 | 7/2011 | Bose et al. |
| 2011/0202085 A1 | 8/2011 | Loganathan |
| 2011/0208227 A1 | 8/2011 | Becking |
| 2011/0265943 A1 | 11/2011 | Rosqueta et al. |
| 2011/0282380 A1 | 11/2011 | Davis et al. |
| 2011/0301686 A1 | 12/2011 | Bowman et al. |
| 2011/0313447 A1 | 12/2011 | Strauss |
| 2011/0319926 A1 | 12/2011 | Becking et al. |
| 2012/0041470 A1 | 2/2012 | Shrivastava et al. |
| 2012/0041472 A1 | 2/2012 | Tan et al. |
| 2012/0046687 A1 | 2/2012 | Trommeter et al. |
| 2012/0065720 A1 | 3/2012 | Strauss |
| 2012/0101510 A1 | 4/2012 | Lenker et al. |
| 2012/0226305 A1 | 9/2012 | Strauss |
| 2012/0316598 A1 | 12/2012 | Becking et al. |
| 2012/0330347 A1 | 12/2012 | Becking et al. |
| 2013/0066360 A1 | 3/2013 | Becking et al. |
| 2013/0085520 A1 | 4/2013 | Liang |
| 2013/0085522 A1 | 4/2013 | Becking et al. |
| 2013/0123830 A1 | 5/2013 | Becking et al. |
| 2013/0138136 A1 | 5/2013 | Beckham |
| 2013/0211495 A1 | 8/2013 | Halden |

(56) References Cited

U.S. PATENT DOCUMENTS

FOREIGN PATENT DOCUMENTS

| | | | |
|---|---|---|---|
| CN | 101234034 A | 8/2008 |
| DE | 19547617 | 9/1997 |
| EP | 717969 A2 | 6/1996 |
| EP | 829236 | 3/1998 |
| EP | 853 955 | 7/1998 |
| EP | 996372 | 5/2000 |
| EP | 1400208 A1 | 3/2004 |
| EP | 1487526 | 12/2004 |
| EP | 1738698 A2 | 1/2007 |
| EP | 832 607 | 4/2008 |
| JP | 09-149904 | 6/1997 |
| JP | 10-201766 | 8/1998 |
| JP | 2004/073874 A | 3/2004 |
| JP | 2004-267749 A | 9/2004 |
| JP | 2006-051349 A | 2/2006 |
| JP | 2009-533202 A | 9/2009 |
| WO | WO-92/21400 | 12/1992 |
| WO | WO-93/11719 | 6/1993 |
| WO | WO-94/06502 A2 | 3/1994 |
| WO | WO-98/34546 | 8/1998 |
| WO | WO-98/58590 | 12/1998 |
| WO | WO-01/58382 | 8/2001 |
| WO | WO-02/054943 A2 | 7/2002 |
| WO | WO-2007/070797 A2 | 6/2007 |
| WO | WO-2007/121405 | 10/2007 |
| WO | WO-2008/085606 | 7/2008 |
| WO | WO-2008/112435 | 9/2008 |
| WO | WO-2010/009019 | 1/2010 |
| WO | WO-2010/117883 | 10/2010 |
| WO | WO-2010/123821 | 10/2010 |

\* cited by examiner

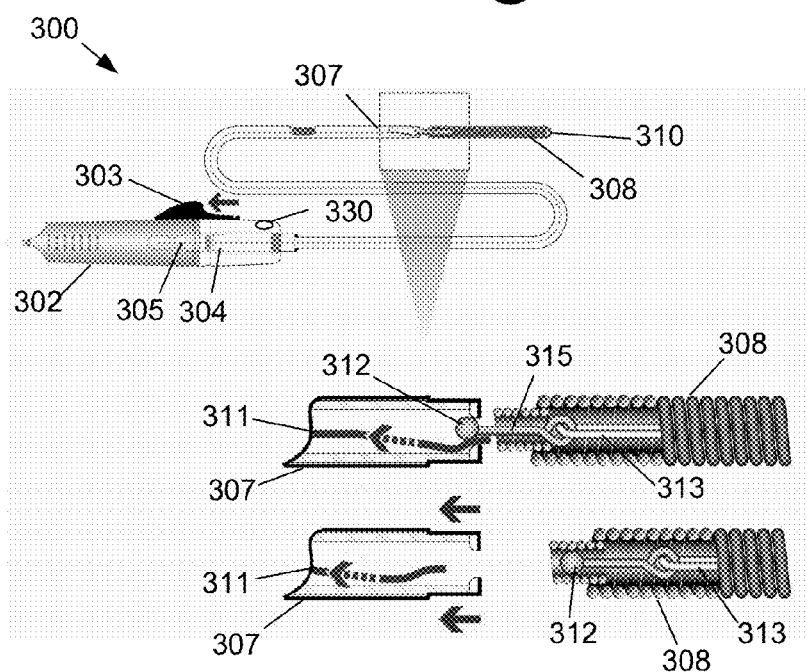

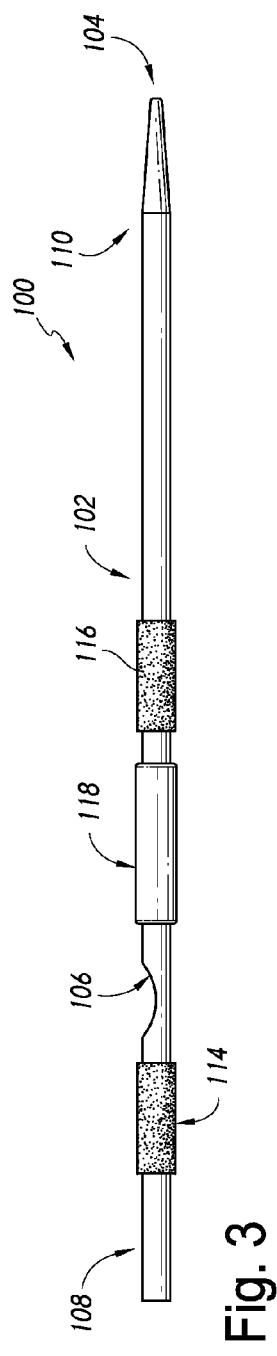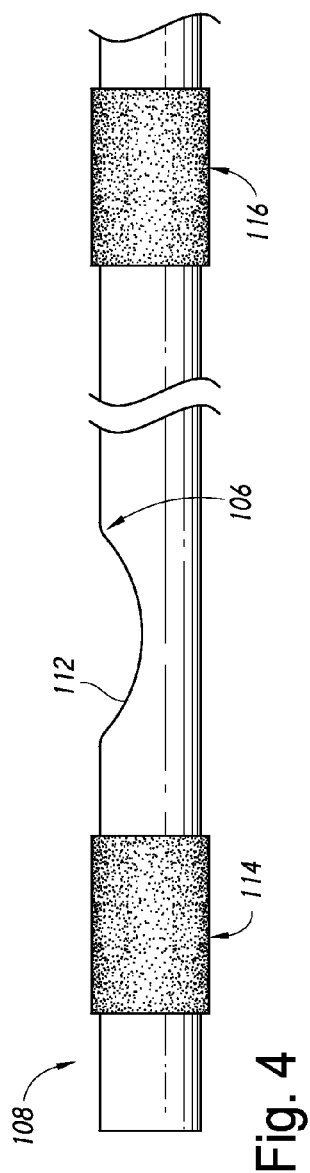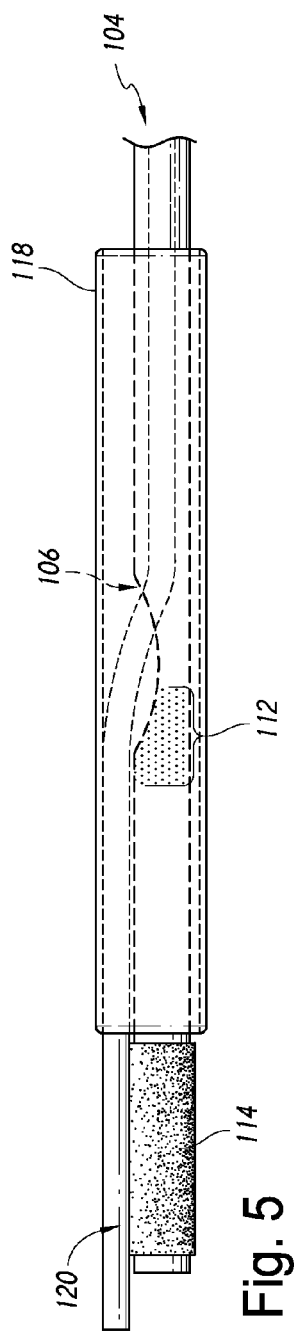

DELIVERY SYSTEM FOR IMPLANTABLE DEVICES

BACKGROUND

The present application generally relates to a delivery system for implantable devices for use within a patient's body and, more particularly, relates to a delivery system for implanting devices in a patient's vasculature.

Lumens in the body can change in size, shape, and/or patency, and such changes can present complications or affect associated body functions. For example, the walls of the vasculature, particularly arterial walls, may develop pathological dilatation called an aneurysm. Aneurysms are observed as a ballooning-out of the wall of an artery. This is a result of the vessel wall being weakened by disease, injury or a congenital abnormality. Aneurysms have thin, weak walls and have a tendency to rupture and are often caused or made worse by high blood pressure. Aneurysms can be found in different parts of the body; the most common being abdominal aortic aneurysms (AAA) and the brain or cerebral aneurysms. The mere presence of an aneurysm is not always life-threatening, but they can have serious health consequences such as a stroke if one should rupture in the brain. Additionally, a ruptured aneurysm can also result in death.

Various approaches have been implemented to treat intravascular or intraluminal complications, such as those described above with aneurysms. Because many of these approaches involve percutaneous treatment, which often requires remote treatment, care is taken to properly place the implantable device in appropriate relation to the complication being treated. Improper placement can result in ineffective treatment and can sometimes lead to injury of the patient being treated.

SUMMARY

According to some embodiments, a medical device for treating a vascular condition comprises a sheath, an elongate delivery member, and a lock. The sheath has a wall that comprises an outer surface and an inner surface, and an opening in the wall. The sheath further has a proximal portion moveable from a first angular position to a second angular position relative to a longitudinal axis of a distal portion of the sheath. The delivery member extends within a lumen of the sheath and through the opening. The delivery member is displaceable along the longitudinal axis. The lock is slidably disposed along the outer surface. The lock slidably moves from a first lock position to a second lock position along the longitudinal axis. When the lock moves from the first lock position to the second lock position, the proximal portion moves from the first angular position to the second angular position and restricts movement of the delivery member relative to the sheath.

According to some embodiments, a medical device for treating a vascular condition comprises a sheath, an elongate delivery member, and a lock. The sheath has a wall comprising an inner surface and an outer surface. The inner surface defines a lumen along the sheath. The sheath has an access opening in a proximal portion of the wall and in fluid communication with the lumen. The delivery member is at least partially disposed within the lumen and passes through the access opening. The lock is slidably disposed along the outer surface. The lock slidably moves from a first position to a second position along a longitudinal axis of the sheath. The lock being positioned in the first position contacts a portion of the delivery member disposed proximal to the access opening, and outside the sheath, such that the lock restricts movement of the delivery member relative to the sheath.

According to certain embodiments, a medical device for treating a vascular condition comprises a sheath, an elongate delivery member, and a lock. The sheath has a wall that comprises an inner surface and an outer surface. The inner surface defines a lumen along the sheath. An access opening is in a proximal portion of the wall and is in fluid communication with the lumen. The delivery member is at least partially disposed within the lumen. The delivery member passes through the access opening. The lock is slidably disposed on an outer periphery of the wall. The lock slidably moves from a first position to a second position along a longitudinal axis of the sheath. The lock positioned in the first position restricts movement of the delivery member.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

FIGS. 1B-1D illustrate embodiments of a device detachment system utilized with an elongate delivery member and medical device, including close up views of attached (B) and detached (C) states for the medical device;

FIG. 3 is an illustration of embodiments of a device for delivery of an occluding device to treat aneurysms with a lock in a first position.

FIG. 4 is a partial detail view of embodiments of FIG. 3.

FIG. 5 is a partial detail view of embodiments of FIG. 2 with the lock in a second position.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

One method of treating aneurysms is to provide an occluding device within the lumen proximate to the aneurysm in order to reduce the likelihood of the aneurysm rupturing. One such occlusion device is a coil. One type of current delivery system for implanting occluding devices in a patient's body include a "wave" lock. The "wave" lock has a series of undulations or "waves" in a sheath of the delivery system. An elongate delivery member disposed within the sheath is contacted by the undulations in the sheath, to help secure the delivery member in a given position. In order to more easily move the delivery member, a practitioner may apply an axial force to the sheath in order to straighten the sheath and reduce the undulations, thereby allowing the delivery member to be more readily moved. However, it has been found that the "wave" lock does not provide very precise control of an amount of effort required to move the delivery member within the sheath. It has also been found that, over time, the "wave" lock may not be as effective as intended, with diminished reliability if not used for several years after manufacturing. Thus, a need exists for an improved delivery system for implanting occluding devices in a patient's body.

Figure 1A:
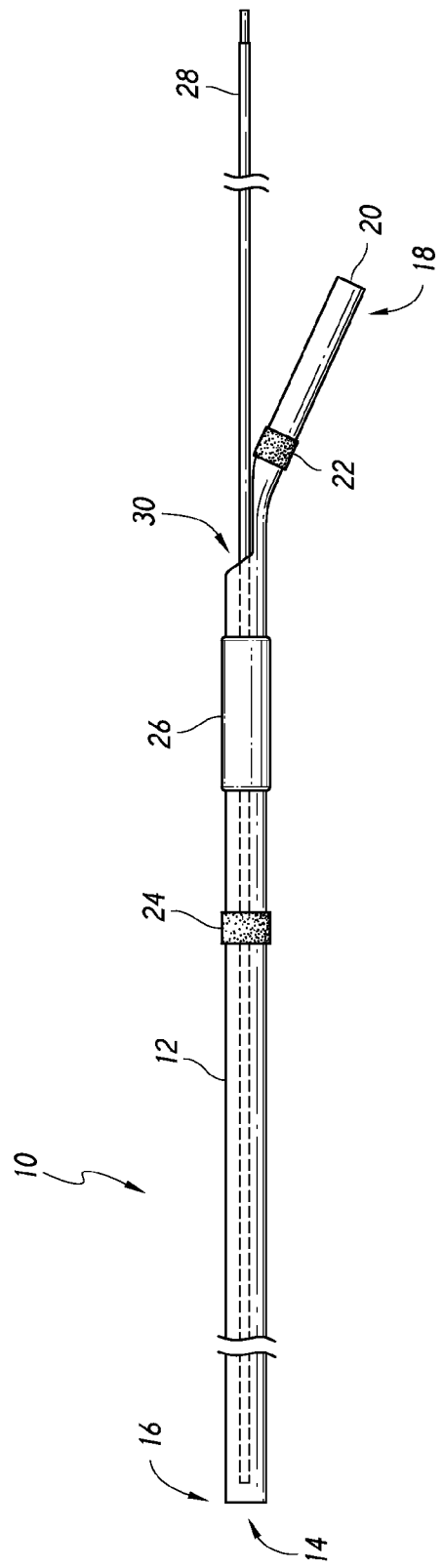
FIG. 1A is an illustration of embodiments of a device for delivery of an occluding device to treat aneurysms with a lock in a first position.
Figure 2:
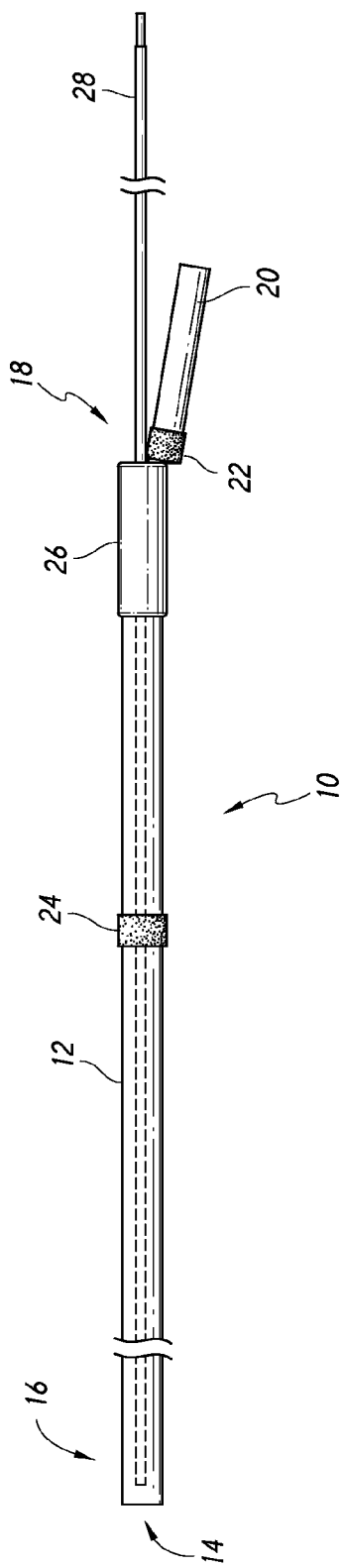
FIG. 2 is an illustration of embodiments shown in FIG. 1 with the lock in a second position.

According to one embodiment, an occluding device delivery assembly 10 is provided as shown in FIGS. 1A-2. The occluding device delivery assembly 10 is adapted to deliver an occluding device within vasculature of an individual undergoing treatment.

With reference to FIG. 1A, the occluding device delivery assembly 10 comprises a thin-walled sheath 12 having an inner wall and an outer wall. A passageway 14, or lumen, is formed through the sheath 12 inside of the inner wall of the sheath 12. The passageway 14 runs from an opening 30 formed proximate a proximal end 18 of the sheath 12 to a distal end 16 of the sheath 12.

A proximal flap 20 is provided at the proximal end 18 of the sheath 12. The proximal flap 20 is moveable from a first position (FIG. 1A) to a second position (FIG. 2) relative to the sheath 12. The proximal flap 20 shown in FIGS. 1A and 2 is integrally formed with the rest of the sheath 12.

Alternatively, it is contemplated that in another embodiment, a proximal flap could be formed as a separate component from a sheath and connected to the sheath. For example the proximal flap may be connected via a hinge to the sheath. Similarly, a fastener or an adhesive may be used to connect the proximal flap to the sheath.

A first marker 22 is disposed on the proximal flap 20 of the sheath 12 proximate a connection of the proximal flap 20 and the sheath 12. The first marker 22 is disposed on an outer surface of the proximal flap 20 of the sheath 12. The first marker 22 protrudes radially outwardly from the proximal flap 20 of the sheath 12. It is contemplated that the first marker 22 extends beyond the outer surface of the proximal flap 20 by from about 0.2 mm to about 0.4 mm.

A second marker 24 is disposed on an outer surface of the sheath 12. The second marker 24 is positioned towards the distal end 16 of the sheath relative to the first marker 22. The second marker 24 protrudes radially outwardly from the outer wall of the sheath 12. It is contemplated that the second marker 24 extends beyond the outer surface of the sheath 16 by from about 0.2 mm to about 0.4 mm.

A slidable lock 26 is disposed on the outer surface of the sheath 12. The slidable lock 26 is positioned between the first marker 22 and the second marker 24 on the sheath 12. The slidable lock 26 is moveable on the outer surface of the sheath 12 between the first marker 22 and the second marker 24. The portion of the first marker 22 and the second marker 24 that protrudes radially outwardly from the proximal flap 20 and the sheath 12, respectively, constrain the movement of the slidable lock 26. The slidable lock 26 as an opening formed therethrough to allow the slidable lock 26 to move about the sheath. The diameter of the opening of the slidable lock 26 is larger than the outer diameter of the sheath 12. It is contemplated that the diameter of the opening of the slidable lock 26 is from about 0.05 mm to about 0.2 mm larger than the outer diameter of the sheath 12.

FIG. 1A shows the slidable lock 26 in an unlocked position. With the slidable lock 26 in the unlocked position, the proximal flap 20 is allowed to move relative to the remainder of the sheath 12. The movement of the proximal flap 20 is generally relative to a longitudinal axis of the sheath 12. In such a configuration, an elongate delivery member 28 is able to pass through an opening 30 formed proximate the proximal end 18 of the sheath 12 and be moved relatively freely within the passageway 14 of the sheath 12. The movement of the slidable lock 26 towards the distal end 16 of the sheath 12 is limited by the position of the second marker 24.

With the slidable lock 26 in the unlocked position, the clinician is able to advance the delivery member 28 to deliver the occluding devices to the site of the aneurysm within the patient.

In the following description, some embodiments of medical device delivery systems are referenced as coil detachment or delivery systems. The scope of the present disclosure, however, is not limited to use with coils, and any other medical devices that may be positioned in a patient, including other vasculature or other luminal body structure, by systems and/or or methods according to the present disclosure. Although embodiments described herein discuss principles of the present disclosure in connection with one or more of these specific applications, these specific applications are provided to illustrate the general principles of the disclosure that can be used with other applications, devices, and procedures. Examples of medical devices that can be implanted include, but are not limited to, embolic coils, stents, urethral implants, and the like.

FIGS. 1B-1D depict an example of a medical device delivery system 300 with an indicator 330 for indicating detachment or release of a medical device. FIG. 1B shows a partial cross section of the delivery system, which is shown, by way of example, as an embolic coil detachment system, having a housing 302 that receives proximal ends of an elongate delivery member 304, having a lumen and which also can be referred to as a pusher or pusher tube, and an elongate core member 305, the distal ends of which are connected to an embolic coil 308. Close up views of the distal ends of the delivery member 304 and core member 305 are shown in FIG. 1C and FIG. 1D, showing attached and detached states for the embolic coil 308, respectively. The elongate delivery member 304 corresponds to the elongate delivery member 28 that is received within and moves relative to the sheath 12 of FIG. 1A.

The device delivery system 300 is configured to receive the delivery member 304 and core member 305 at proximal ends of both relative to the device delivery system 300, with the coil 308 located at the distal ends of each. The device delivery system 300 includes a user-input mechanism 303 that receives an input signal from a user and relays the input signal to a grasping mechanism of the device delivery system 300. The user input mechanism 303 functions to allow the user to cause detachment of the coil 308 at the distal end of the core member 305 by triggering the grasping mechanism to displace the proximal end of the core member 305 relative to the proximal end of the delivery member 304.

Regarding the user input mechanism 303, any suitable mechanism may be used that allows a user-supplied input signal to initiate the displacement of the proximal end of the core member 305 relative to the proximal end of the delivery member 304 to effect detachment of the embolic coil 308. In this way, a user, such as a surgeon, can cause detachment of the coil 308 at a desired time, such as when the coil has been placed at a desired location within a patient's vasculature to treat an aneurysm. Examples for the user input mechanism 303 can include, but are not limited to, thumb slides, mechanical switches, electromechanical switches, magnetic switches, electromagnetic switches, and/or combinations of such. User input mechanisms 303 may produce any type of suitable signals to initiate displacement of the proximal end of the core member 305 relative to the proximal end of the delivery member 304; such signals may be mechanical, electrical, magnetic, optical, RF, or any other type of signal and may be analog or digital. The user input signal can be initiated by any suitable user input modality, e.g., a button, a capacitive touch sensor, a keyboard, a moveable slide, and the like.

As indicated in FIG. 1C, embolic coil 308 is releasably held to the distal end of the core member 307 and the distal end of the delivery member 307. Such a releasable connection may be achieved, as shown, by a ball end 312 at the end of a link 315, which is configured within the coil 308 and connected to an end cap 310 by way of a non-stretchable link 313, e.g., made of polypropylene or other suitable material. When the user input mechanism 303 is activated by the user, e.g., as when the slide in FIG. 1B is moved in the direction shown by the arrow, the distal end 311 of the core member 304 is moved away from the ball end 312, releasing the embolic coil 308 as shown in FIG. 1D. The coil 308 is then detached from the distal end of the delivery member 307 and the core member 304.

Positioning of the medical device, which is shown by way of example as a coil 308 in FIGS. 1B-1D, is often a concern for physicians during such procedures. Relative movement between the medical device, the elongate delivery member 28, a core member 305 (if used in the system), and the sheath 12 can introduce uncertainty in positioning of the medical device within the vasculature or other body lumen. FIG. 1 illustrated how the elongate delivery member 28 is received by the sheath 12 and is moveable within a lumen of the sheath 12. Described below are embodiments for securing the elongate delivery member 28 within the sheath 12 to reduce relative movement, which can assist in reducing uncertainty during positioning of the medical device being delivered.

FIG. 2 shows the slidable lock 26 in a locked position. With the slidable lock 26 in the locked position, the proximal flap 20 is moved towards the longitudinal axis of the sheath 12. The slidable lock 26 is moved towards the proximal end 18 of the sheath 12 and covers, or at least partially covers, the opening 30 where the delivery member 28 enters the passageway 14 of the sheath 12. The first marker 22 contacts the delivery member 28. The proximal flap 20 also contacts the delivery member 28 with the slidable lock 26 in the locked position. The contact between the first marker 22 and the proximal flap 20 with the delivery member 28 restricts the movement of the delivery member 28 within the passageway 14 of the sheath 12. Thus, with the slidable lock 26 in the locked position, the delivery member 28 may only be moved with a great deal of effort by the clinician.

It is contemplated that a variety of materials may be used in the occluding device delivery assembly 10. For example, the sheath 12 typically comprises at least one polymeric material. It is also contemplated that the sheath 12 may be formed from multiple polymeric materials, such as can be accomplished in a co-extrusion manufacturing process. For instance it is contemplated that the sheath 12 may be made from at least one of polypropylene (PP) and high density polyethylene (HDPE). It is also contemplated that the sheath 12 may include an inner portion that comprises HDPE, and an outer portion that comprises PP. It is further contemplated that the sheath 12 may also comprise a colorant.

The slidable lock 26 may also comprise a polymeric material. For instance, the slidable lock 26 may comprise HDPE. It is also contemplated that the slidable lock 26 comprise a colorant. The colorant of the slidable lock 26 is different than the colorant of the sheath 12, so that a contrast exists between the sheath 12 and the slidable lock 26. For instance, the sheath 12 may have a violet colorant, and the slidable lock 26 may have a yellow colorant.

The markers 22, 24 may comprise a polymeric material. For instance the markers may comprise polyethylene terephthalate (PET).

While the occluding device delivery assembly 10 is depicted as having two markers 22, 24, it is contemplated that in an alternate embodiment a occluding device delivery assembly may be provided with only a proximal marker. The proximal marker positions the slidable lock 26 relative to the proximal flap 20 to control the position of the proximal flap 20.

While the occluding device delivery assembly 10 is depicted as having two markers 22, 24, it is contemplated that in an alternate embodiment at least one stop for the slidable lock 26 may be formed on the sheath 12. For instance the sheath 12 may be provided with a region with a larger outer diameter that limits the movement of the slidable lock 26 on the sheath 12.

Turning to FIGS. 3-5, another embodiment of an occluding device delivery assembly 100 is depicted.

The occluding device delivery assembly 100 comprises a thin-walled sheath 102 having an inner wall and an outer wall. A passageway 104, or lumen, is formed through the sheath 102, inside of the inner wall of the sheath 102. The passageway 104 runs from an opening 106 formed proximate a proximal end 108 of the sheath 102 to a distal end 110 of the sheath 102. The opening 106 provides access to the passageway 104 of the sheath 102.

A seal 112 is provided at a proximal end of the opening 106 of the sheath 102. The seal 112 closes off the passageway 104 towards the proximal end 108 of the opening 106. Thus, the passageway 104 extends from the opening 106 to the distal end 110 of the sheath 102. It is contemplated that the seal 112 may be integrally formed with the sheath 102, but it is contemplated that the seal 112 could be formed as a separate component from the sheath 102 and placed within the opening 106 in the sheath 102 via a fastener, an adhesive, or the like.

A first marker 114 is disposed on a proximal side of the opening 106 of the sheath 102. The first marker 114 being disposed on an outer surface of the sheath 102. The first marker 114 protrudes radially outwardly from the sheath 102.

A second marker 116 is disposed on an outer surface of the sheath 102. The second marker 116 is positioned towards the distal end 110 of the sheath 102 relative to the first marker 114. The second marker 116 protrudes radially outwardly from the outer wall of the sheath 102. The second marker 116 is positioned distally from the opening 106 in the sheath 102.

A slidable lock 118 is disposed on the outer surface of the sheath 102. The slidable lock 118 is positioned between the first marker 114 and the second marker 116 on the sheath 102. The slidable lock 118 is moveable on the outer surface of the sheath 102 between the first marker 114 and the second marker 116. The portion of the first marker 114 and the second marker 116 that protrude radially outwardly from the sheath 102 constrain the movement of the slidable lock 118.

FIG. 3 shows the slidable lock 118 in an unlocked position. With the slidable lock 118 in the unlocked position, the opening 106 in the sheath 102 is fully exposed. In such a configuration, an elongate delivery member 120 (FIG. 5) is able to pass through the opening 106 formed proximate the proximal end 108 of the sheath 102 and be moved relatively freely within the passageway 104 of the sheath 102. The movement of the slidable lock 118 towards the distal end 110 of the sheath 102 is limited by the position of the second marker 116.

With the slidable lock 118 in the unlocked position, the clinician is able to advance the delivery member 120 to deliver the occluding devices to the site of the aneurysm within the patient.

FIG. 5 shows the slidable lock 118 in a locked position. The slidable lock 118 is moved towards the proximal end 108 of the sheath 102 and covers, or at least partially covers, the opening 106 where the delivery member 120 enters the passageway 104 of the sheath 102. The delivery member 120 contacts the slidable lock 118 and the outer surface of the sheath 102 proximate the opening 106. The contact between the delivery member 120 and the slidable lock 118 and the sheath 102 restricts the movement of the delivery member 120 within the passageway 104 of the sheath 102. Thus, with the slidable lock 118 in the locked position, the delivery member 120 may only be moved with a great deal of effort by the clinician.

It is contemplated that the slidable lock 118 may be made from a polymeric material, such as HDPE. The slidable lock 118 may be made from a compressible material so that the slidable lock 118 may be positioned over the sheath 102 and the delivery member 120 disposed outside of the sheath, as shown in FIG. 5, and form a press fit that constrains the delivery member 120 between the sheath 102 and the slidable lock 118.

It is contemplated that the sheath 102 may have an inner diameter of from about 0.3 mm to about 0.6 mm and an outer diameter of from about 0.6 mm to about 0.9 mm. It is additionally contemplated that the sheath 102 may be made from a polymeric material. Materials that may be utilized to form the sheath 102 include, but are not limited to, polypropylene (PP) and high density polyethylene (HDPE). It is further contemplated that the sheath 102 may be formed from layers of different polymeric materials, such as an inner layer of HDPE and an outer layer of PP. It is further contemplated that a dye or colorant be added to the HDPE layer of the sheath 102, such as a purple dye, to enhance the clinician's ability to see the sheath 102.

It is contemplated that the slidable lock 118 may have an inner diameter of from about 0.7 mm to about 1.0 mm and an outer diameter of from about 1.3 mm to about 1.6 mm. The slidable lock 118 may have a length of about 25 mm according to one embodiment. It is additionally contemplated that the slidable lock 118 may be made from a polymeric material. One material that may be utilized to form the slidable lock 118 is HDPE. It is further contemplated that a dye or colorant be added to the slidable lock 118. It is contemplated that the dye or colorant added to the slidable lock 118 may contrast the dye or colorant added to the sheath 102, such as a yellow dye to enhance the visibility of the slidable lock 118 relative to the sheath 102.

It is contemplated that the markers 114, 116 may comprise a polymeric material. For instance the markers 114, 116 may comprise polyethylene terephthalate (PET).

While the occluding device delivery assembly 100 is depicted as having two markers 114, 116, it is contemplated that in an alternate embodiment at least one stop for the slidable lock 118 may be formed on the sheath 102. For instance the sheath 102 may be provided with a region with a larger outer diameter that limits the movement of the slidable lock 118 on the sheath 102 in the proximal direction.

While the occluding device delivery assembly 100 is depicted as having two markers 114, 116, it is contemplated that in an alternate embodiment an occluding device delivery assembly may be provided with only a proximal marker. The proximal marker positions the slidable lock 118 relative to the opening 106 of the sheath 112.

The apparatus and methods discussed herein are not limited to the deployment and use of an occluding device within the vascular system but may include any number of further treatment applications. Other treatment sites may include areas or regions of the body such as organ bodies. Modification of each of the above-described apparatus and methods for carrying out the subject technology, and variations of aspects of the disclosure that are apparent to those of skill in the art are intended to be within the scope of the claims. Furthermore, no element, component or method step is intended to be dedicated to the public regardless of whether the element, component or method step is explicitly recited in the claims.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations which will be apparent to those skilled in the art may be made in the arrangement, operation and details of the method and apparatus of the subject technology disclosed herein without departing from the spirit and scope of the subject technology as defined in the appended claims. Therefore, the scope of the subject technology should be determined by the appended claims and their legal equivalents. Furthermore, no element, component or method step is intended to be dedicated to the public regardless of whether the element, component or method step is explicitly recited in the claims. Underlined and/or italicized headings and subheadings are used for convenience only, do not limit the subject technology, and are not referred to in connection with the interpretation of the description of the subject technology. In the claims and description, unless otherwise expressed, reference to an element in the singular is not intended to mean "one and only one" unless explicitly stated, but rather is meant to mean "one or more." In addition, it is not necessary for a device or method to address every problem that is solvable by different embodiments of the disclosure in order to be encompassed by the claims.

What is claimed is:

1. A medical device delivery system, comprising:
   a sheath having a wall comprising an inner surface and an outer surface, the inner surface defining a lumen along the sheath, an access opening through a proximal portion of the outer surface and in fluid communication with the lumen, the access opening separated from a proximal end of the sheath;
   a delivery member at least partially disposed within a portion of the lumen distal to the access opening, the delivery member passing through the access opening;
   a lock slidably disposed on an outer periphery of the wall, the lock slidably moveable between a first position and a second position along a longitudinal axis of the sheath; and
   a first marker disposed proximal to the opening on the outer surface, the first marker protruding radially outwardly from the sheath, the first marker preventing movement of the lock towards a proximal end of the sheath beyond the first position;

wherein the first marker is positioned such that, when the lock is in the first position, the lock covers the access opening and restricts proximal and distal longitudinal movement of the delivery member relative to the sheath.

2. The system of claim 1, wherein:

a proximal portion of the sheath is moveable from a first angular position to a second angular position relative to the longitudinal axis of the sheath; and when the lock moves from the second position to the first position, the proximal portion of the sheath moves from the first angular position to the second angular position and restricts movement of the delivery member relative to the sheath.

3. The system of claim 1, wherein the first marker contacts the delivery member with the lock in the first position.

4. The system of claim 1, further comprising a second marker disposed on the outer periphery of the sheath, the second marker protruding radially outwardly from the outer periphery of the sheath, the second marker being positioned distally relative to the first marker, the second marker limiting movement of the lock towards the distal end of the sheath.

5. The system of claim 4, wherein the second marker is about 130 mm from the first marker.

6. The system of claim 1, wherein the sheath comprises a polymeric material.

7. The system of claim 6, wherein the polymeric material comprises at least one of polypropylene or high density polyethylene.

8. The system of claim 1, wherein the lock comprises a polymeric material.

9. The system of claim 8, wherein the polymeric material comprises high density polyethylene.

10. The system of claim 1, wherein the lumen has a diameter of from about 0.3 mm to about 0.6 mm.

11. The system of claim 1, wherein the sheath has an outer diameter of from about 0.6 mm to about 0.9 mm.

12. The system of claim 1, wherein the lock in the first position contacts a portion of the delivery member disposed proximal to the access opening.

13. A medical device delivery system, comprising:

a sheath having a wall comprising an inner surface and an outer surface, the inner surface defining a lumen along the sheath, an access opening through a proximal portion of the wall and in fluid communication with the lumen, the access opening spaced distally from a proximal end of the sheath;

a delivery member at least partially disposed within a portion of the lumen distal to the access opening, the delivery member passing through the access opening;

a lock slidably disposed along the outer surface, the lock slidably moveable between a first position and a second position along a longitudinal axis of the sheath; and a first marker disposed proximal to the opening on the outer surface, the first marker protruding radially outwardly from the sheath, the first marker limiting movement of the lock towards a proximal end of the sheath beyond the first position;

wherein the first marker is positioned such that, when the lock is in the first position, the lock covers the access opening and contacts a portion of the delivery member disposed proximal to the access opening, and outside the sheath, such that the lock restricts proximal and distal longitudinal movement of the delivery member relative to the sheath.

14. The system of claim 13, further comprising a second marker disposed distal to the access opening on the outer surface, the second marker protruding radially outwardly from the outer surface, the second marker limiting movement of the lock towards a distal end of the sheath.

15. The system of claim 14, wherein the second marker is disposed about 130 mm from the first marker.

16. The system of claim 13, wherein the portion of the delivery member disposed proximal to the access opening additionally contacts the outer surface.

17. The system of claim 13, wherein the sheath comprises a polymeric material.

18. The system of claim 17, wherein the polymeric material comprises at least one of polypropylene or high density polyethylene.

19. The system of claim 13, wherein the lock comprises a polymeric material.

20. The system of claim 19, wherein the polymeric material comprises high density polyethylene.

21. The system of claim 13, wherein the lumen has a diameter of from about 0.3 mm to about 0.6 mm.

22. The system of claim 13, wherein the sheath has an outer diameter of from about 0.6 mm to about 0.9 mm.

* * * * *